(12) United States Patent
Bijl et al.

(10) Patent No.: US 7,431,952 B2
(45) Date of Patent: Oct. 7, 2008

(54) ISOLATION OF MICROBIAL OILS

(75) Inventors: Hendrik Louis Bijl, Vlaardingen (NL); Albert Schaap, Barendrecht (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/343,861

(22) PCT Filed: Aug. 1, 2001

(86) PCT No.: PCT/EP01/08903

§ 371 (c)(1), (2), (4) Date: Oct. 10, 2003

(87) PCT Pub. No.: WO02/10423

PCT Pub. Date: Feb. 7, 2002

(65) Prior Publication Data

US 2004/0067574 A1    Apr. 8, 2004

(30) Foreign Application Priority Data

Aug. 2, 2000    (EP) .................................. 00306601

(51) Int. Cl.
*A01N 63/02* (2006.01)
*A01N 65/00* (2006.01)
*A01N 63/04* (2006.01)
*C12P 1/00* (2006.01)
*C12P 7/64* (2006.01)

(52) U.S. Cl. ............. 424/780; 424/195.15; 424/195.16; 435/41; 435/134

(58) Field of Classification Search ............. 424/283.1; 435/41, 134, 170, 171
See application file for complete search history.

(56) References Cited

U.S. PATENT DOCUMENTS

| | | | |
|---|---|---|---|
| 4,720,456 A | 1/1988 | Wagner et al. | 435/74 |
| 5,130,242 A | 7/1992 | Barclay | 435/134 |
| 5,179,012 A | 1/1993 | Gudin et al. | 435/125 |
| 5,338,673 A | 8/1994 | Thepenier et al. | 435/134 |
| 5,539,133 A | 7/1996 | Kohn et al. | 554/20 |
| 5,897,994 A | 4/1999 | Sandoz et al. | 435/134 |
| 5,928,696 A | 7/1999 | Best et al. | 426/417 |
| 6,750,048 B2 | 6/2004 | Ruecker et al. | 435/134 |

FOREIGN PATENT DOCUMENTS

| | | | |
|---|---|---|---|
| GB | 808 128 | | 1/1959 |
| GB | 808128 A | * | 1/1959 |
| WO | WO 97/04121 | * | 2/1997 |
| WO | WO 9704121 A1 | * | 2/1997 |
| WO | WO 97/36996 | * | 10/1997 |
| WO | WO 97/37032 | | 10/1997 |
| WO | WO 9736996 A2 | * | 10/1997 |
| WO | WO 98/03671 | | 1/1998 |
| WO | WO 98/50574 | | 11/1998 |
| WO | WO 99/32604 | | 7/1999 |
| WO | WO 01/53512 | | 7/2001 |
| WO | WO 01/53512 A1 | * | 8/2001 |

OTHER PUBLICATIONS

Hruschka et al (Ocl-Oleagineux Corps Gras Lipides, (Sep.-Oct. 1998)), vol. 5, No. 5, p. 356-360 (Abstract only)).*
Database WPI Section Ch, Week 198904; Derwent Publications Ltd., London, GB, AN 1989-029582 XP002205925 & JP 63 0304990 A (Agency of Ind Sci & Technology), Dec. 13, 1988 Abstract.
Graille, J. et al., "Biotechnology of Lipids: Some Possible Applications" Oleagineux 43(4):181-190 (1988).
Preez, du, J.C. et al., "Production of Gamma-Linolenic Acid by Mucor Circinelloides and Mucor Rouxii with Acetic Acid as Carbon Substrate" Biotechnology Letters 17(9):933-938 (1995).
Vazhappilly, R. et al., "Eicosapentaenoic Acid and Docosahexaenoic Acid Production Potential of Microalgae and their Heterotrophic Growth" Journal of the American Oil Chemists' Society 75(3):393-397 (1998).

* cited by examiner

*Primary Examiner*—N. M. Minnifield
*Assistant Examiner*—Vanessa L. Ford
(74) *Attorney, Agent, or Firm*—Nixon & Vanderhye P.C.

(57) ABSTRACT

The extraction of a microbial or single cell oil, for example comprising one or more polyunsaturated fatty acids (PUFAs), directly from microbial cells is disclosed which avoids the need for solvents. After fermentation, the microbial cells are pasteurised, washed and the cell walls lysed or disrupted by a mechanical (e.g. homogenisation), physical (boiling or drying), chemical (solvents) or enzymatic (cell wall degrading enzymes) technique. The oil (containing the PUFA) is then separated from the resulting cell wall debris. This is achieved by centrifugation, which results in an oily phase (top layer) that contains the oil which that can be separated from an aqueous phase (containing the cell wall debris). The oil can then be extracted and if necessary the PUFA can be purified or isolated from the oil.

51 Claims, No Drawings

ISOLATION OF MICROBIAL OILS

This application is a 371 of PCT/EP01/08903 filed Aug. 1, 2001.

The present invention relates to the extraction (and then isolation) of a microbial (or single cell) oil, preferably comprising one or more polyunsaturated fatty acids (PUFAs), from single cell (or micro-) organisms. The process of the invention involves the disruption or lysis of microbial cell walls, followed by separating the oil from the resulting cell debris. The invention additionally relates to a microbial oil recovered by this process, preferably having a PUFA.

Polyunsaturated fatty acids, or PUFAs, are found naturally and a wide variety of different PUFAs are produced by different single cell organisms (algae, fungi, etc). They have many uses, for example inclusion into foodstuffs (such as infant formula), nutritional supplements and pharmaceuticals.

In most microbial PUFA production processes a microorganism is first cultured in a fermenter in a suitable medium. The microbial biomass is then harvested and treated to enable subsequent extraction of a lipid from the biomass with a suitable solvent. The lipid is usually subjected to several refining steps. Care must be taken during the process because degradation can occur if the lipids are subjected to lipolysis or oxidising conditions, for example heating (in the presence of oxygen) and/or due to lipases or lipoxygenases. The art teaches that to avoid oxidation (such as resulting from breaking open the cells and so exposing the contents to oxygen) PUFAs can be extracted from whole intact cells using a solvent (see WO-A-97/36996 and WO-A-97/37032). The use of solvents is a common way of removing lipids from microbial biomass (WO-A-98/50574).

Although these extraction processes have been used for several years, the solvent needs to be removed and this results in extra cost. In addition, if the lipid is to be used in a foodstuff, it is important that certain solvents, such as hexane, are removed completely, or only remain in very small quantities. If the hexane is removed by evaporation then this may involve heating, and that not only adds to costs but can cause lipid degradation. Furthermore, with increasing environmental considerations, the use of solvents for the extraction of lipids is becoming increasingly expensive and unpopular.

The present invention therefore seeks to solve or at least mitigate these problems. The applicant has found that lipids, such as those comprising a PUFA, can be efficiently extracted from microbial cells without the need for solvent(s).

Therefore, according to a first aspect of the present invention there is provided a process for obtaining an oil (or fat or lipid, the terms are used interchangeably) from microbial cells, the process comprising (a) disrupting (or lysing) the cell walls (of the microbial cells) to release (or liberate) an oil from the cells. The (microbial or single cell) oil can then be (b) separated from at least part of the resulting cell wall debris. One can then (c) recover, purify and/or isolate the (microbial) oil (or one or more PUFAs). A good yield of the oil can be achieved using this process without the need for a solvent. Preferably the oil will comprise a PUFA, namely one or more PUFAs. Preferably this process (including stages (a) and (b)) is solvent-free.

Recent PUFA preparation processes advocate keeping the microbial cells intact (WO-A-97/36996). This publication describes a PUFA production process where a microbial biomass is generated by fermenting a microorganism, and following fermentation the cells are heated. Water is removed from the biomass, and the resulting material extruded to form porous granules. The PUFA is then extracted from the intact cells inside the granules by contact with a solvent, usually hexane. The hexane is then evaporated to produce a crude oil. Throughout this process the cells are kept intact to prevent oxygen in the atmosphere contacting the PUFAs as it was thought that this would cause undesirable oxidation. However, it has now been found that a good quality PUFA oil can be achieved if the cells are in fact lysed: any potential oxidation by the atmosphere can be more than compensated by the advantage of avoiding the need for solvents.

PUFAs and Microorganisms

The PUFA can either be a single PUFA or two or more different PUFAs. If there are 2 or more PUFAs then either each PUFA or the total amount of all the PUFAs is within the amounts specified (e.g. a total PUFA content of no more than 0.1 g/kg feed).

The or each PUFA can be of the n-3 or n-6 family. Preferably it is a C18, C20 or C22 PUFA or a PUFA with at least 18 carbon atoms and 3 double bonds. The PUFA(s) can be provided in the form of a free fatty acid, a salt, as a fatty acid ester (e.g. methyl or ethyl ester), as a phospholipid and/or in the form of a mono-, di- or triglyceride.

Suitable (n-3 and n-6) PUFAs include:
docosahexaenoic acid (DHA, 22:6 omega-3), suitably from algae or fungi, such as the (dinoflagellate) Crypthecodinium or the (fungus) Thraustochytrium;
γ-linolenic acid (GLA, 18:3 omega-6);
α-linolenic acid (ALA, 18:3 omega-3);
conjugated linoleic acid (octadecadienoic acid, CLA);
dihomo-γ-linolenic acid (DGLA, 20:3 omega-6);
arachidonic acid (ARA, 20:4 omega-6); and
eicosapentaenoic acid (EPA, 20:5 omega-3).

Preferred PUFAs include arachidonic acid (ARA), docosohexaenoic acid (DHA), eicosapentaenoic acid (EPA) and/or γ-linoleic acid (GLA). In particular, ARA is preferred.

The PUFAs may be from a natural (e.g. vegetable or marine) source or may be derived from a single cell or microbial source. Thus the PUFA may be of (or from) microbial, algal or plant origin (or source). In particular, the PUFA may be produced by a bacteria, fungus or yeast. Fungi are preferred, preferably of the order Mucorales, for example *Mortierella, Phycomyces, Blakeslea, Aspergillus, Thraustochytrium, Pythium* or *Entomophthora*. The preferred source of ARA is from *Mortierella alpina, Blakeslea trispora, Aspergillus terreus* or *Pythium insidiosum*. Algae can be dinoflagellate and/or include *Porphyridium, Nitszchia*, or *Crypthecodinium* (e.g. *Crypthecodinium cohnii*). Yeasts include those of the genus *Pichia* or *Saccharomyces*, such as *Pichia ciferii*. Bacteria can be of the genus *Propionibacterium*.

In the process of the invention the microbial cells (or microorganisms) can first be suitably cultured or fermented, such as in a fermenter vessel containing an (e.g. aqueous) culture medium. The fermentation conditions may be optimised for a high oil and/or PUFA content in the resulting biomass. If desirable, and for example after fermentation is finished, the microorganisms may be killed and/or pasteurised. This may be to inactivate any undesirable enzymes, for example enzymes that might degrade the oil or reduce the yield of the PUFAs.

The fermentation broth (biomass and culture medium) may then be removed (e.g. let out) from the fermenter, and may be passed to cell-wall disrupting equipment (e.g. a homogeniser). If necessary liquid (usually water) can (firstly) be removed therefrom. Any suitable solid liquid separation technique can be used. This (dewatering) may be by centrifugation and/or filtration. The cells may be washed, for example using an aqueous solution (such as water) for example to remove any extracellular water-soluble or water-dispersible compounds. The cells may then be ready for disruption or lysis.

Cell Lysis (Stage (a))

The cell walls of the microbial cells can then be disrupted (or lysed). This can be achieved using one or more enzymatic, physical or mechanical methods or techniques, for example at high shear conditions. Physical techniques include heating and/or drying the cells to a sufficient temperature whereby the cell walls are ruptured. This may comprise boiling.

Enzymatic methods include lysis by one or more enzymes, e.g. cell wall degrading enzymes. The cell wall degrading enzyme may be a lytic enzyme. Other enzymes include (e.g. alkaline) proteases, cellulases, hemicellulases, chitinases and/or pectinases. Other cell wall degrading substances may be used instead of or in combination with one or more enzymes, e.g. salts, alkali, and/or one or more surfactants or detergents. A combination of physical, mechanical and/or enzymatic methods is also contemplated.

If a mechanical technique is employed this may comprise homogenisation, for example using a homogeniser. This may be a ball mill or any other machine able to disrupt the cell walls. Suitable homogenizers include high pressure homogenizers (for example at a pressure of 300 to 500 kg/cm$^2$ or bar) such as a polytron homogenizer. Other homogenization techniques may involve mixing with particles, e.g. sand and/or glass beads (e.g. use of a bead mill). Alternative mechanical techniques include the use of milling apparatus, for example homoblenders. Other methods of disrupting the cell walls include ultrasound, spray drying and/or pressing or appliance of high pressure. This last technique is called cold-pressing: it may be performed at pressures of 100 to 600 or 700 bar (Atm or kg/cm$^2$), such as 150-500 bar, optimally from 200-400 bar.

Homogenization is the preferred method of disrupting the cell walls. There may be from 1 to 3 passes through the homogeniser, either at high and/or low during disruption (e.g. homogenisation) pressures. For example one may use a Gaulin™ homogenizer. The pressure may be from 300 to 900, such as 400 to 800, and optimally 500 to 600 or 700 bar (Atm or kg/m$^2$). Lower pressures may be employed if required, e.g. from 150 to 300 bar. Hence working pressures can vary from 150 to 900 bar depending on the type of homogeniser, number of passes, etc.

Although cell lysis can be performed chemically this is preferably not employed as (this stage in) the process is desireably solvent-free.

The disruption of the cell walls may be performed either on the broth resulting from fermentation, for example the cells may still be contained in culture medium or such medium may be present. One or more additives my be added or present (swuch as analkali metal salt, e.g. NaCl) during disruption or may be added after disruption (e.g. to a homogenised broth). During disruption an organic solvent (e.g. meOH, cloroform) is preferably not present. The disruption may be performed on the (optionally washed and/or concentrated) biomass (e.g following solid liquid separation). Disruption is therefore performed on an (e.g. aqueous) composition comprising the cells and water but not containing a solvent.

In order to improve cell wall disruption, disruption may be performed at a dry matter content of about 10 to 200 g/l. This may be on the fermentation broth, for example after fermentation, or it may be derived from the broth, for example after the broth has been subjected to de-watering and/or solid/liquid separation.

If necessary a separation inducer, to encourage separation of the oil from the debris, may be added at this stage, to the homogenised material.

Separation of Oil from Cell Debris (Stage (b))

The microbial oil is then separated from at least part of the cell wall debris formed. At this stage there may be in an oily or lipid phase or layer (and this may comprise the PUFA). This may be a top or upper layer. This layer can be above a (lower) aqueous layer, e.g. containing cell wall debris. The oily layer (comprising the PUFA) can then be separated from the aqueous layer (or phase). One or more surfactants or detergents may be present or added to assist this process.

The separation of the oil from at least some of the cell wall debris is preferably achieved or assisted by using a mechanical method, in particular by centrifugation. Suitable centrifuges can be obtained from Westfalia™ (semi- and industrial scale) or Beckman™ (e.g. laboratory centrifuges). Centrifugation (e.g. for a laboratory scale centrifuge) may last for from 2 or 4 to 8 or 15, such as from 3 or 5 to 7 or 12, optimally from 4 or 5 to 6 or 10 minutes (residence time).

The centrifugal force (g) may be from 1,000 or 2,000 to 10,000 or 25,000, such as from 3,000 or 5,000 to 8,000 or 20,000, optimally from 4,000 to 6,000 g, or from 7,000 to 9,000 g, although centrifugation can be employed at g-forces up to 12,000 g, 15,000 g, 20,000 g or 25,000 g. Centrifugation may be at 4,000 to 14,000 rpm such as 6,000 to 12,000 rpm, optimally at from 8,000 to 10,000 rpm. One or more centrifugations may be necessary. The maximum g force may be lower if using certain centrifuges, for example this may be 6000 g if using a Westfalia™ centrifuge (e.g. model NA-7). The flow rate may be from 100-500 liters/hour, such as 150 to 450 l/hr, optimally from 200 to 400 l/hr. Centrifugation may result in either a 2-phase system (a fatty or oily top layer and a lower aqueous layer) or a 3-phase system (a fatty or oily top layer, a middle aqueous layer and a bottom layer, usually containing the cell debris).

A separation inducer, or agent that aids separation, may be added. This may be present or supplemented during (a) or after (a) (but before (b), or during (b). This may aid the formation of separate oily and aqueous phases. The inducer may increase the density of the aqueous phase, which may then become even more dense than the oily phase. Suitable inducers include alkali metal salts, e.g. NaCl. The inducer may be added at a concentration of 10-150 g/l, such as 30-130 g/l, optimally from 50-100 g/l.

The oil may be free of any carotenoids, e.g. ∃-carotene. Following disruption and separation the process of the invention may further comprise extracting, purifying or isolating the oil or one or more PUFAs.

Solvent Avoidance

One advantage of the process of the invention is that one can avoid the need for solvent. (In this context solvent excludes water, since the culture medium is usually aqueous and the cells may be washed with water). Thus, no (e.g. organic) solvent(s) may be employed either during disruption of the cell walls in (a), or in the separation of the PUFA from at least part of the cell wall debris, in (b). Preferably, no (e.g. organic) solvent is used either in the extraction, purification or isolation of the oil or one or more PUFAs. Thus, in essence, the process can be solvent-free. Thus stages (a), (b) and optionally also (c) can be performed without an (e.g. organic) solvent, for example without the need of a solvent for the oil (or PUFA), e.g. an alkane such as hexane, an alcohol (e.g. methanol) or a haloalkane (e.g. chloroform).

Preferably, the use of a surfactant can also be avoided, and each or both of the disruption and separation stages (a) and (b)

can also be performed without the need of a surfactant, for example in the absence of any detergents.

A second aspect of the invention relates to an oil preparable (or prepared) by a process of the first aspect.

If the oil comprises a PUFA, then the PUFA is preferably predominantly (such as greater than 50%, 70% or even 90% or 95%) in the form of triglycerides. The oil may have one or more of the following characteristics (or components):

(a) sterols, e.g. desmosterol, or cell debris such as from 0.01 to 1.0%, e.g. 0.05 to 0.5%, preferably from 0.1 to 0.2%;
(b) phospholipids or triglycerides, such as from 0.1 to 2.0%, e.g. from 0.3 to 1.5%, preferably from 0.5 to 1.0%; and/or
(c) diglycerides at no more than 0.1, 0.05 or 0.001%. The oil may be refined and/or treated with an acid and/or alkali if required.

The PUFA (or oil containing a PUFA) may be subjected to further downstream processing, for example degumming, neutralisation, bleaching, deodorization, or winterization.

Overall Protocol

A preferred process of the present invention therefore comprises:
(a) culturing microbial cells, for example under conditions whereby they produce a microbial oil or at least one PUFA;
(b) optionally heating or pasteurising the cells, for example to kill the cells and/pr to inactivate any undesirable enzymes;
(c) optionally removing an (aqueous) liquid (such as dewatering), for example by centrifugation, filtration or a suitable solid-liquid separation technique;
(d) optionally, washing the microbial cells, for example with water, preferably to remove extracellular water-soluble or water-dispersible compounds;
(e) disrupting or lysing the cell walls of the microbial cells, for example by a physical, enzymatic or mechanical technique (such as homogenisation, e.g. with an homogeniser or a ball mill). This can release some of the oil and/or PUFA present in the microbial cells. The (mechanical) disruption may be supplemented with or substituted by chemical and/or enzymatic disruption. A separation inducer (for example to aid formation of two layers, in the next stage, may be added);
(f) separation of the microbial oil (or PUFA) from the cell wall debris, for example formation and then separation of an oil phase from the resultant cell wall debris and/or aqueous phase. This may comprise centrifugation, optionally with the addition of one or more salts, a pH shift (towards alkaline), and may involve the presence of one or more cell degrading enzymes, surfactants or emulsifiers. One can obtain an (e.g. upper) oil phase and an (e.g. lower) aqueous phase. The oil phase may contain the PUFA. The aqueous phase may contain cell debris;
(g) extraction, purification or isolation of the oil (or of the PUFA from the oil phase), for example resulting in a PUFA-containing oil; and
(h) optionally acid treatment (or degumming), alkali treatment (or neutralisation), bleaching, deodorising, cooling (or winterisation). This may remove undesirable substances such as free fatty acids (FFAs), proteins, phospholipids, trace metals, pigments, carbohydrates, soaps, oxidation products, sulphur, pigment decomposition products, sterols, saturated triglycerides and/or mono- or di-glycerides.

The heat treatment or pasteurization preferably inactivates or denatures one or more oil (or PUFA) degrading enzymes.

The temperature of heating may be from 70 to 90° C., such as about 80° C. It may inactivate or denature enzymes such as lipases and/or lipoxygenases.

One may add one or more (e.g. water and/or oil-soluble) antioxidants, for example vitamin C, ascorbyl palmitate and/or tocopherol, and this may be done after stage (b), or at a later stage for example after extraction, such as before or after any refining (step (h) above).

There may be one or more additional heating steps, for example to remove other undesirable compounds or components. For example, heating may take place at an acid pH, for example to remove components such as phospholipids, trace metals, pigments, carbohydrates and/or proteins. Here the temperature may be from 50 to 80° C., such as 55 to 75° C., optimally from 60 to 70° C. The pH may be from 1 to 6, such as 2 to 5, optimally at a pH from 3 to 4. This can result in degumming and/or removal of proteins and/or water-soluble or water-dispersible compounds.

Alternatively or in addition a further heating step, this time at alkaline pH, may employed. The pH may be from 8 to 13, such as from 9 to 12, optimally at a pH of from 10 to 11. The temperature may be the same as that described in the previous paragraph.

Features or characteristics of one aspect of the invention are applicable to another aspect mutatis mutandis.

Equipment (Industrial Process Plant)

A third aspect of the invention reltes to apparatus for conducting the process of the first aspect. The third aspect may thus comprise:
(a) means for culturing (or fermenting) microbial cells (e.g. a fermenter), optionally linked to;
(b) means for disrupting (or lysing) cell walls of the microbial cells (e.g. a homogeniser), optionally linked to;
(c) means for separating a (resulting) oil from (resulting) cell debris The cells and culture medium (e.g. broth) may be passed directly to the means in (b). Each of the means can be positioned in the order specified, icroning the order of the stages of the process of the first aspect. Means for performing any or all of the disruption and separation steps as described earlier may be provided, for example means to add a separation inducer (e.g. to homogenised material), or for performing any of the steps described in the overall protocol (e.g. eating/pasteurising means, solid-liquid separation means, etc).

EXAMPLE 1

Preparation of Crude PUFA (ARA) Oil from a Fermentation Broth of *Mortierella alpina*

A fermentation broth of *Mortierella alpina* (previously pasteurized at 65° C. for one hour) containing arachidonic acid (ARA) was homogenized once by means of an MC-4 APV Gaulin™ homogenizer at 600 bar (600 Atm) to disrupt the cell walls. NACl was added to the homogenized broth to a final concentration of 100 g/l. Subsequently the homogenized broth was centrifuged by means of a Sorval RC 5B centrifuge for 10 minutes at 9,000 rpm (equivalent to about 20,000 g) resulting in an arachidonic acid-enriched oily top layerand a lower aqueous layer containing the cell debris. Crude PUFA oil was recovered.

The yield of oil was 9% (based on the oil in the cell). The (oil) layer had the following approximate composition: 0.1% desmosterols; 0.7% phospholipids; 6.7% triglycerides; 0.1% diglycerides, 70% water and 20% medium components and cell debris.

The invention will now be described, by way of example, with reference to the following Examples which are provided by way of illustration only.

EXAMPLE 2

Preparation of Crude PUFA (ARA) Oil from a Fermentation Broth of *Mortierella alpina*

A fermentation broth of *Mortierella alpina* (previously pasteurized at 65° C. for 1 hour) containing arachidonic acid (ARA) was homogenized once by means of an MC-4 APV Gaulin™ homogenizer at 600 bar (600 Atm) to disrupt the cell walls. Subsequently the homogenized broth was centrifuged by means of a Westfalia™ NA-7 disc centrifuge at maximum speed (about 8,000 rpm, equivalent to about 8,000 g at the disc stack) resulting in an arachidonic acid-enriched oily top layer (that was recovered from the centrifuge) and a lower aqueous layer containing the cell debris. A crude PUFA oil was recovered: the yield of oil was 95% (based on the oil in the cell). The crude oil had the following approximate composition: 1 to 2% sterols and cell debris; 3 to 4% phospholipids; 4% monoglycerides; 6% diglycerides; and the remainder being triglycerides.

EXAMPLE 3

Preparation of Crude PUFA (DHA) Oil from a Fermentation Broth of *Cryptecodinium cohnii*

Following fermentation 20 liters of fermentation broth (pasteurised at 65° C. for one hour) of the algae *Cryptheco-dinium cohnii* was homogenized three times by means of an APV Gaulin™ homogenizer (type: Lab 60/60-10 TB SX), each time at 600 bar, to lyse the algal cell walls. Subsequently NaCl was added to the homogenized broth to a final concentration of 50 g/l. Oil was recovered using a labscale centrifuge (Beckman™ JM/6E) by centrifuging the broth in 800 ml portion s each for 5 minutes at 5,000 g. This resulted in a DHA-enriched fatty top layer (crude oil) and a lower aqueous layer. Crude oil was recovered from the fatty top layer.

EXAMPLE 4

Preparation of Crude PUFA (DHA) Oil from a Fermentation Broth of *Crypthecodinium cohnii*

Following fermentation 20 liters of a fermentation broth (pasteurised at 65° C. for 1 hour) of the algae *Crypthecod-inium cohnii* was homogenized three times by means of an of APV Gaulin™ homogenizer (type: Lab 60/60-10 TB SX), each time at 600 bar (600 ATm), to lyse the algal cell walls. Subsequently a crude oil was recovered using a labscale centrifuge (Beckman™ JM/6E) by centrifuging the broth in 800 ml portions each for 5 minutes at 5000 g. This resulted in a DHA-enriched fatty top layer (crude oil) and a lower aqueous layer. A crude PUFA oil was recovered from the fatty top layer.

The invention claimed is:

1. A process for obtaining an oil from microbial cells, the oil comprising one or more polyunsaturated fatty acids (PUFAs), the process comprising:
   (a) disrupting the cell walls of microbial cells to release the oil, wherein the disrupting comprises homogenizing said cells; and
   (b) separating, by centrifugation, the oil from cell wall debris formed in (a), wherein the separating step does not comprise the step of separating by extracting the oil from the cell wall debris with a solvent.

2. The process of claim 1 which, after step (b), further comprises:
   (c) extracting, purifying or isolating the microbial oil or one or more PUFAs.

3. The process of claim 1 wherein the separating results in the formation of an oily layer that comprises a microbial oil or a PUFA and an aqueous layer.

4. The process of claim 3 wherein the oily layer is an upper layer above the aqueous layer.

5. The process of claim 1 wherein PUFA is C18, C20, C22, omega-3 or omega-6.

6. The process of claim 1 wherein the microbial cells are yeast, bacterial, fungal or algal cells.

7. The process of claim 1 wherein steps (a) and/or (b) are performed free of any organic solvent(s).

8. The process of claim 2 wherein step (c) is performed free of any organic solvent(s).

9. The process of claim 1 which further comprises, before step (a), culturing or fermenting microbial cells under conditions that allow production of the oil.

10. The process of claim 1 wherein the disrupting of step (a) comprises treating said cells with one or more cell wall degrading enzymes or surfactants.

11. The process of claim 1 wherein the separating of step (b) comprises treating with a separation inducer.

12. The process of claim 1, wherein the disrupting comprises homogenization at a pressure from 150 to 900 bar.

13. The process of claim 1, which further comprises, before step (a), pasteurizing and/or heating the cells.

14. The process of claim 1, wherein one or more surfactants are presented during (b).

15. The process of claim 6, wherein the microbial cells are from *Mortierella alpina, Phycomyces, Blakeslea, Aspergillus, Pythium, Entomophthora, Porphyridium, Nitszchia, Pichia, Saccharomyces,* or *Propionibacterium.*

16. A process for obtaining an oil from microbial cells, the oil comprising one or more polyunsaturated fatty acids (PUFAs), the process comprising:
   (a) disrupting the cell walls of microbial cells to release the oil, wherein the disrupting comprises homogenizing said cells; and
   (b) separating, by centrifugation and addition of a separation inducer to aid formation of an oily layer comprising the oil and an aqueous layer, the oil from cell wall debris formed in (a) thereby resulting in separate oily and aqueous layers;
   wherein no solvent for extraction of the oil is employed in steps (a) and (b).

17. The process of claim 16, wherein the disrupting comprises homogenization at a pressure from 150 to 900 bar.

18. The process of claim 16 which, after step (b), further comprises:
   (c) extracting, purifying or isolating the microbial oil or one or more PUFAs.

19. The process of claim 18 wherein step (c) is performed free of any organic solvent(s).

20. The process of claim 16 wherein the oily layer is an upper layer above the aqueous layer.

21. The process of claim 16 wherein the PUFA is C18, C20, C22, omega-3 or omega-6.

22. The process of claim 16 wherein the microbial cells are yeast, bacterial, fungal or algal cells.

23. The process of claim 22, wherein the microbial cells are from *Mortierella alpina, Phycomyces, Blakeslea, Aspergil-*

*lus, Pythium, Entomophthora, Porphyridium, Nitszchia, Pichia, Saccharomyces*, or *Propionibacterium*.

24. The process of claim 16 wherein steps (a) and/or (b) are performed free of any organic solvent(s).

25. The process of claim 16 which further comprises, before step (a), culturing or fermenting microbial cells under conditions that allow production of the oil.

26. The process of claim 16 wherein the disrupting of step (a) comprises treating said cells with one or more cell wall degrading enzymes or surfactants.

27. The process of claim 16, which further comprises, before step (a), pasteurizing and/or heating the cells.

28. The process of claim 16, wherein one or more surfactants are present during (b).

29. A process for obtaining an oil from microbial cells, the oil comprising one or more polyunsaturated fatty acids (PUFAs), the process comprising:
   (a) disrupting the microbial cells by at least homogenization to release the oil and to form cell wall debris therefrom,
   (b) separating the oil from the cell wall debris by at least centrifugation and addition of a separation inducer to aid formation of an oily layer comprising the oil and an aqueous layer to form separate oily and aqueous layers, and
   (c) extracting the oil from the cell wall debris without using an organic solvent.

30. The process of claim 29, wherein the disrupting comprises homogenization at a pressure from 150 to 900 bar.

31. The process of claim 29 wherein the oily layer is an upper layer above the aqueous layer.

32. The process of claim 29 wherein the PUFA is C18, C20, C22, omega-3 or omega-6.

33. The process of claim 29 wherein the microbial cells are yeast, bacterial, fungal or algal cells.

34. The process of claim 33, wherein the microbial cells are from *Mortierella alpina, Phycomyces, Blakeslea, Aspergillus, Pythium, Entomophthora, Porphyridium, Nitszchia, Pichia, Saccharomyces*, or *Propionibacterium*.

35. The process of claim 29 wherein steps (a) and/or (b) are performed free of any organic solvent(s).

36. The process of claim 29 which further comprises, before step (a), culturing or fermenting microbial cells under conditions that allow production of the oil.

37. The process of claim 29 wherein the disrupting of step (a) comprises treating said cells with one or more cell wall degrading enzymes or surfactants.

38. The process of claim 29, which further comprises, before step (a), pasteurizing and/or heating the cells.

39. The process of claim 29, wherein one or more surfactants are present during (b).

40. The process of claim 1, wherein the oil comprises arachidonic acid.

41. The process of claim 40, wherein the microbial cells are from *Mortierella alpina, Blakeslea trispora, Aspergillus terreus* or *Pythium insidiosum*.

42. The process of claim 41, wherein the microbial cells are from *Mortierella alpina*.

43. The process of claim 16, wherein the oil comprises arachidonic acid.

44. The process of claim 16, wherein the microbial cells are from *Mortierella alpina, Blakeslea trispora, Aspergillus terreus* or *Pythium insidiosum*.

45. The process of claim 44, wherein the microbial cells are from *Mortierella alpina*.

46. The process of claim 29, wherein the oil comprises arachidonic acid.

47. The process of claim 46, wherein the microbial cells are from *Mortierella alpina, Blakeslea trispora, Aspergillus terreus* or *Pythium insidiosum*.

48. The process of claim 47, wherein the microbial cells are from *Mortierella alpina*.

49. The process of claim 16, wherein the separation inducer is NaCl.

50. The process of claim 29, wherein the separation inducer is NaCl.

51. The process of claim 29, wherein the separation inducer increases the density of the aqueous layer to become more dense than the oily layer.

\* \* \* \* \*